United States Patent
Castellanos (10) Patent No.: US 10,925,580 B2
(45) Date of Patent: *Feb. 23, 2021

(54) MOBILE VASCULAR HEALTH EVALUATION DEVICES USING DOPPLER ULTRASOUND AND CORRELATION OF PARAMETERS TO OUTPUT RECOMMENDATIONS TO A WRIST-MOUNTED DISPLAY

(75) Inventor: Alexander F. Castellanos, Templeton, CA (US)

(73) Assignee: Alexander Francis Castellanos 2002 Trust, Templeton, CA (US)

( * ) Notice: Subject to any disclaimer, the term of this patent is extended or adjusted under 35 U.S.C. 154(b) by 854 days.

This patent is subject to a terminal disclaimer.

(21) Appl. No.: 13/598,371

(22) Filed: Aug. 29, 2012

(65) Prior Publication Data
US 2013/0053655 A1    Feb. 28, 2013

Related U.S. Application Data

(60) Provisional application No. 61/528,518, filed on Aug. 29, 2011.

(51) Int. Cl.
| A61B 8/00 | (2006.01) |
| A61B 8/06 | (2006.01) |
| A61B 8/08 | (2006.01) |
| A61B 5/02 | (2006.01) |
| A61B 5/00 | (2006.01) |
| A61B 5/0205 | (2006.01) |

(52) U.S. Cl.
CPC .......... *A61B 8/4427* (2013.01); *A61B 5/0022* (2013.01); *A61B 5/0205* (2013.01); *A61B 5/02007* (2013.01); *A61B 8/06* (2013.01); *A61B 8/488* (2013.01); *A61B 8/565* (2013.01); *A61B 8/485* (2013.01)

(58) Field of Classification Search
None
See application file for complete search history.

(56) References Cited

U.S. PATENT DOCUMENTS

| 4,601,292 A | 7/1986 | Fidel et al. |
| 4,745,924 A | 5/1988 | Ruff |
| 4,802,458 A | 2/1989 | Finsterwald et al. |
| 4,860,759 A | 8/1989 | Kahn et al. |
| 4,967,753 A | 11/1990 | Haase et al. |
| 5,195,519 A | 5/1993 | Angelsen |
| 5,277,187 A | 1/1994 | Pillsbury |
| 5,357,427 A | 10/1994 | Langen et al. |
| 5,409,009 A | 4/1995 | Olson |
| 5,409,010 A | 4/1995 | Beach et al. |
| 5,529,073 A | 6/1996 | Kielbasiewicz |
| 5,666,404 A | 9/1997 | Ciccotelli et al. |
| 6,319,201 B1 | 11/2001 | Wilk |
| 6,454,712 B1 | 9/2002 | Oonuki |
| 6,612,985 B2 | 9/2003 | Eiffert et al. |
| 6,712,762 B1 | 3/2004 | Lichter et al. |
| 7,074,183 B2 | 7/2006 | Castellanos |
| 7,733,224 B2 * | 6/2010 | Tran ....................... G16H 15/00 340/540 |
| 2001/0032099 A1 | 10/2001 | Joao |
| 2002/0035316 A1 | 3/2002 | Drazen |
| 2002/0183599 A1 | 12/2002 | Castellanos |
| 2004/0127798 A1 | 7/2004 | Dala-Krishna et al. |
| 2007/0276270 A1 | 11/2007 | Tran |

OTHER PUBLICATIONS

Keller et al., "Noninavasive Angiography for the Carotid Artery Disease Using Doppler Ultrasound", dated 1976, pp. 354-363.
U.S. Appl. No. 13/733,079, filed Jan. 2, 2013, Final Office Action, dated Dec. 3, 2015.
Hartley, Carolyn P. et al., "A New Look at Disease Management," The Physician's eHealth Report, vol. 2.6 Nov./Dec. 2005, 12 pages.
Haynes, R et al., "Interventions to enhance medication adherence," Abstract, Cochrane Database Syst Rev Oct. 19, 2005; (4):CD000011.
Kaushik, R et al., "Biofeedback assisted diaphragmatic breathing and systematic relaxation versus propranolol in long term prophylaxis of migraine," Abstract, Complement Ther Med Sep. 2005;13(3):165-74.
Krueger, KP et al., "Improving adherence and persistence: a review and assessment of interventions and description of steps toward a national adherence initiative," Abstract, J Am Pharm Assoc (Wash DC), Nov.-Dec. 2003; 43(6):668-78.
McDonald, HP et al., "Interventions to enhance patient adherence to medication prescriptions: scientific review," Abstract, JAMA Dec. 11, 2002; 288(22):2868-79.
McGinnis, RA et al., "Biofeedback-assisted relaxation in type 2 diabetes," Abstract, Diabetes Care Sep. 2005:28(9):2145-9.
Medicine Avenue, Inc., products description, located on the internet at <http://www.healtheheart.com>, retrieved on Jan. 3, 2004, 2 pages.
Nolan, RP et al., "Heart rate variability biofeedback as a behavioral neurocardiac intervention to enhance vagal heart rate control," Abstract, 1: Am Heart J Jun. 2005:149(6):1137.
Pittler, MH et al., "Complementary therapies for peripheral arterial disease: systematic review," Abstract, 1 Atherosclerosis Jul. 2005; 181(1):1-7, Mar. 31, 2005.

(Continued)

*Primary Examiner* — G Steven Vanni
(74) *Attorney, Agent, or Firm* — Hickman Becker Bingham Ledesma LLP (57) ABSTRACT

A mobile measurement device comprising a computing device; one or more sensors that are coupled to the computing device using one or more corresponding compatible digital interfaces; and logic encoded with instructions which when executed perform determining and storing vascular function information and one or more of: values of metrics or parameters; physiological analysis of the parameters and the vascular function information; recommendations for actions that an individual or healthcare provider should take in response to the recommendations or parameters. Embodiments further include processes for using vascular function information collected from a mobile measurement device to generate the parameters, analysis, and recommendations.

15 Claims, 3 Drawing Sheets

(56) References Cited

OTHER PUBLICATIONS

Silverman, J., "Partnership Between Physician and Patient is Key to Successful Compliance," 34 eFamily Practice News 1, Jan. 1, 2004, 1 page.
Stefano, GB et al., "Integrative medical therapy: examination of meditation's therapeutic and global medicinal outcomes via nitric oxide (review)," Abstract, Int J Mol Med Oct. 2005:16(4):621-30.
Space Medical, "Products", 1999, 1 page.
Tindle, HA et al., "Factors associated with the use of mind body therapies among United States adults with musculoskeletal pain," Abstract, Complement Ther Med Sep. 2005: 13(3):155-64.
M. Zoler, "Framingham Score Drives Coronary Prevention," 34 eFamily Practice News (Mar. 1, 2004).
K. Rother, "Framingham Heart Study analysis reveals some primary prevention subgroups are being overlooked" (theheart.org, Oct. 2004).
A. Cohen et al., "A categorization and analysis of the criticisms of Evidence-Based Medicine," 11 Int'l J. of Medical Informatics 2 (2003).
Deborah F. Tate PhD, et al., "Using Internet Technology to Deliver a Behavioral Weight Loss Program," JAMA, Mar. 7, 2001, vol. 285, No. 9, p. 1172-1177.
Nancy Walsh, "Meditation Program Linked to Reduction in Carotid Intima-Media Thickness," Mar. 1, 2001, Family Practice News, p. 15.

\* cited by examiner

MOBILE VASCULAR HEALTH EVALUATION DEVICES USING DOPPLER ULTRASOUND AND CORRELATION OF PARAMETERS TO OUTPUT RECOMMENDATIONS TO A WRIST-MOUNTED DISPLAY

CROSS-REFERENCE TO RELATED APPLICATIONS; BENEFIT CLAIM

This application claims the benefit under 35 U.S.C. § 119(e) of provisional application 61/528,518, filed Aug. 29, 2011, the entire contents of which is hereby incorporated by reference as if fully set forth herein.

FIELD OF THE INVENTION

The present disclosure generally relates to medical devices and medical diagnostic methods, and more specifically relates to devices and techniques for assessing health conditions of elements of the vascular system.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

In humans, negative vascular condition has been associated with or is known to be symptomatic with a variety of serious diseases including coronary artery disease and diabetes. For example, reduced elasticity of the coronary arteries may indicate the presence of plaque on the walls of the arteries and may contribute to myocardial infarction. Vascular function information also may be useful in early recognition of sepsis, hypertension, hypotension, or respiratory dysfunction. Accurate measurements of the elasticity, thickness, and mechanical performance of blood vessels in conducting blood flow may permit better evaluation of diseases that are associated with negative vascular health and recommendation of a variety of therapies.

However, in the state of the art, vascular measurements typically require elaborate equipment and can only be performed in a clinical setting on a periodic basis. For example, one typical method involves using Doppler sonography systems to obtain acoustic readings from the peripheral principal arteries from one or more body locations, such as the ankles. The systems are large, expensive, and normally capable of use only in a medical office. Further, these systems normally are not integrated with other valuable measures of personal health.

Devices are available that measure vital signs, blood glucose, gases in the body, respiratory activity, and other aspects of physiology. For example, smartphone applications or "apps" are available to enable an individual to take their pulse using a smartphone, and other apps can take pictures of food and provide readouts of food contents and calories. However, these measurements and apps may be incapable of integrating with other valuable health information or providing a global assessment of healthy or unhealthy status.

SUMMARY OF THE INVENTION

The appended claims may serve as a summary of the invention.

BRIEF DESCRIPTION OF THE DRAWINGS

The present invention is illustrated by way of example, and not by way of limitation, in the figures of the accompanying drawings and in which like reference numerals refer to similar elements and in which.

DESCRIPTION OF EXAMPLE EMBODIMENTS

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Overview of Example Mobile Measurement Devices

Figure 2:
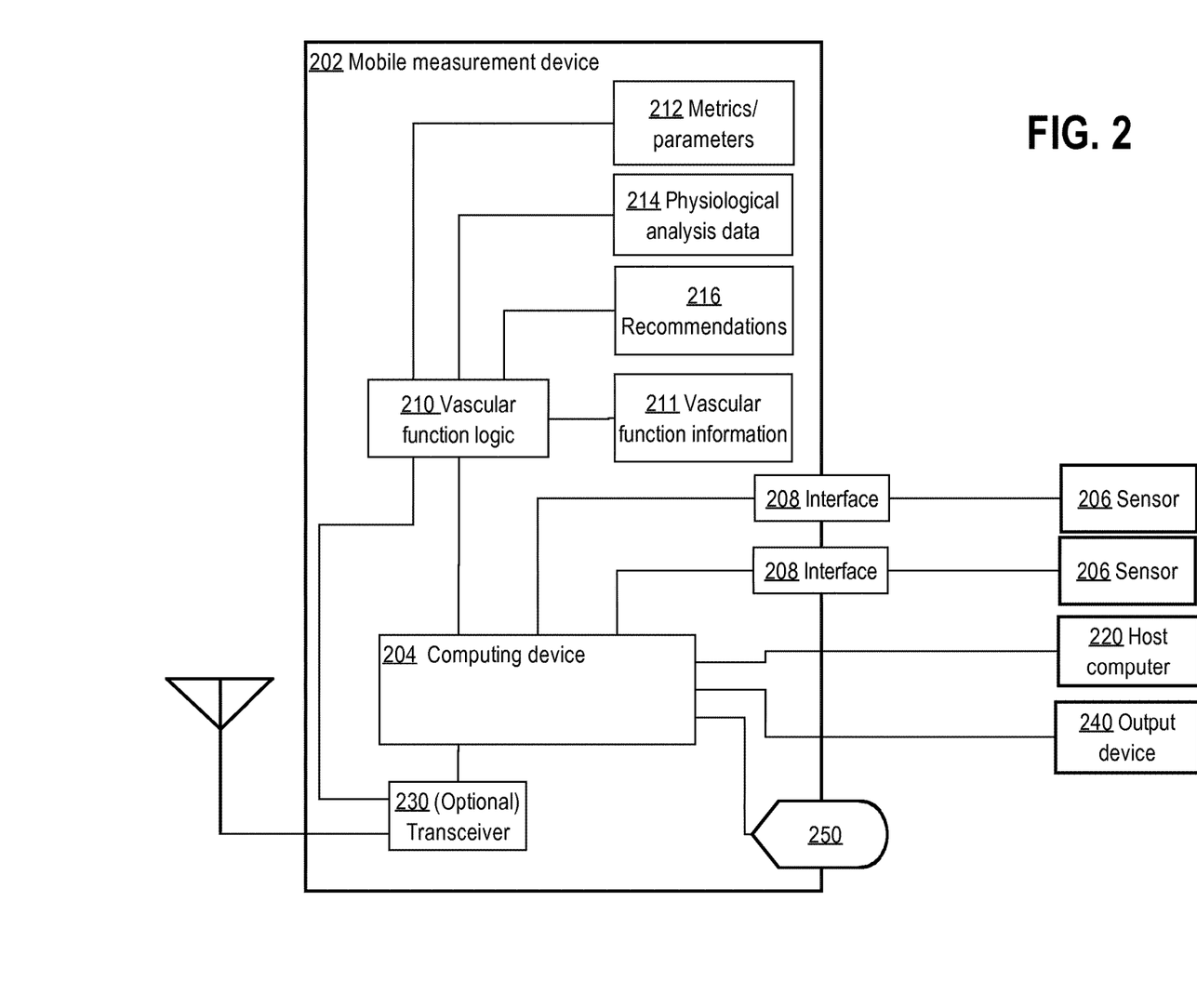
FIG. 2 illustrates an example mobile measurement device.

In an embodiment, a mobile measurement device is configured to process information from the environment and human physiology and anatomy. FIG. 2 illustrates an example mobile measurement device. In an embodiment, the mobile measurement device 202 comprises: a computing device 204; one or more sensors 206 that are coupled to the computing device using one or more corresponding compatible digital interfaces 208; and vascular function logic 210 encoded with instructions which when executed perform determining and storing vascular function information 211 and one or more of: values of metrics or parameters 212; physiological analysis 214 of the parameters and the vascular function information; recommendations 216 for actions that an individual or healthcare provider should take in response to the recommendations or parameters.

In various embodiments, the computing device 202 comprises any of: a smartphone; a tablet computer; a laptop computer or other personal computer; a workstation; a watch computer; a ring-mounted computer; an active steering wheel of a motor vehicle; a hat-mounted computer; a helmet-mounted computer; an eyewear-mounted computer. In other embodiments, the computing device 202 comprises or is integrated with any of: a body garment such as a short, swimsuit, vest, shorts or shoes.

In various embodiments, the sensors 206 comprise at least one of the following: an ultrasound sensor configured to acoustically measure structure, performance or other metrics associated with a blood vessel or other element of the vascular system and to cooperate with the program logic to provide output waveform data representing acoustic measurements of blood flow in a blood vessel, and provide vascular structure or performance metrics 212 based on bidirectional vascular waveform analysis. In an embodiment, one of the sensors 206 or the vascular function logic 210 perform bidirectional waveform Doppler ultrasound analysis that can measure or indicate the elasticity of one or more blood vessels. In an embodiment, the vascular function information 211 comprises or is based on the bidirectional waveform Doppler ultrasound analysis.

In various embodiments, the sensors 206 comprise one or more of any of the following: an infrared, crystal technology, or light-based physiological monitor; a blood pressure sensor; a pulse sensor; a respiratory rate sensor comprising, for example, one or more chest patches, wrist patches, and/or chest straps; a body temperature sensor; an oxygen absorption sensor; a carbon dioxide sensor; a nitric oxide sensor; a blood glucose sensor; a sensor of electrolytes, nutrients in the circulation, or other metrics; one or more contact lenses configured to measure capillary blood flow; a flow meter; a spirometer; a mouthpiece. In an embodiment, at least one of the sensors 206 is configured to sense and store at least one measurement relating to vascular structure, status or performance. Thus, as alternatives to using ultrasound as a form of energy for sensing, in some embodiments sensors that use infrared spectroscopy, auto-fluorescence, GLASS technology and other forms of energy or radiation may be used to obtain vascular waveforms for analysis.

In various embodiments, the vascular function logic 210 comprises one or more of any of the following: non-volatile random access memory (NVRAM); flash memory; an application-specific integrated circuit (ASIC); a field programmable gate array; read-only memory (ROM) including any of electrically erasable ROM (EEROM) or electrically programmable ROM (EPROM); disk storage; any of which may be configured with stored program instructions that are arranged to perform the processes that are further described herein. Wireless devices such as wireless probes may be used as sensors 206.

In various embodiments, the vascular function information 211 provides metrics, reports, or values that indicate overall health attributes of blood vessels or other components of the vascular system, or particular attributes of blood vessels or other components of the vascular system. Examples of attributes include elasticity of vascular walls; thickness of vascular walls; and an indication of whether a heart pulse cycle results in one, two, or three elastic responses of the vascular walls; presence or amount of plaque formation on the vascular walls.

In various embodiments, the vascular function information 211 may be used to generate, using vascular function logic 210 or other program logic, one or more reports, recommendations 216, or protocols based on the vascular function information. Recommendations 216 may collectively and broadly represent reports and protocols as well as recommendations. In various embodiments, the reports, recommendations or protocols may comprise any of the following: a status report on vascular function; a list of options for medical intervention in the patient based on medical standards of practice based on one or more medical indications represented in the vascular function information; reports or recommendations suggesting sepsis, hypertension, hypotension, respiratory dysfunction, kidney function, heart rhythm, hydration level; a protocol for exercise; a protocol for sports performance; a protocol for patient lifestyle or changes in lifestyle; a protocol for patient stress management; a report of recommendations, or the expected effects of, any of several aspects of treatment including but not limited to hydration, nutrition, exercise, supplements, and medications.

In various embodiments, the device 202 may be configured to directly generate the vascular function information 211, and the one or more reports, recommendations, or protocols based on the vascular function information. Alternatively, the device 202 may be activated or used in a clinical setting such as an emergency room, hospital ward or medical office. The device 202 also may be used or activated in non-clinical settings such as during driving a car, during exercise, during sleep, and during other activities. For example, in any of these embodiments, the device 202 may internally generate the vascular function information 211 and also provide logic for interfacing with an external host computer 220 to download the vascular function information; on the host computer, stored program logic may be configured to generate the one or more reports, recommendations, or protocols based on the vascular function information.

In this manner, the device 202 provides a useful interface between the patient and the medical office; the device may be used to collect a variety of physiological metrics from an individual, including at least one measurement of vascular structure, status or performance, which are then downloaded from the device to the host computer 220. After downloading, program logic on the host computer 220 may be used to generate the one or more reports, recommendations, or protocols based on the vascular function information. Data collected over time can be used to better understand factors influencing the cardiovascular system.

Alternatively, after downloading data from the device 202, an independent measurement of at least one measurement of vascular structure, status or performance is performed in association with the host computer. For example, in one approach, an individual uses the device 202 to monitor any of the physiological metrics described above, then downloads the metrics and transfers or provides the metrics to a healthcare provider via host computer 220. In a clinical setting or quasi-clinical setting, the healthcare provider may use a conventional Doppler vascular sensor to capture an acoustic profile of the vascular performance of the same individual; for example, the healthcare provider could perform a Doppler vascular test of the peripheral arteries or arteries at other body locations at which a Doppler vascular signal can be obtained. The resulting acoustic waveform data may be combined with the metrics that have been downloaded from the patient's monitoring device 202 and, under control of program logic at the host computer 220, used to generate the one or more reports, recommendations, or protocols. In various embodiments, the patient may transfer or provide the metrics to the healthcare provider by any of the following: connecting the device 202 to a personal computer that is owned or operated by the patient, downloading a data file from the device, and streaming, e-mailing or uploading the data file to the healthcare provider; going to the premises of the healthcare provider, connecting the device to a host computer that is owned or operated by the healthcare provider, downloading a data file from the device to the host computer.

In various embodiments, the sensors 206 may comprise units that can detect activity of the nervous system either centrally or peripherally. For example, waveform data from an electroencephalogram (EEG) unit may reveal brain activity that can be correlated to vascular waveform data to identify progress in therapeutic goals and/or the condition of the vasculature.

In various embodiments, the data from sensors 206 may be combined with results or detections of blood test measurements for substances such as cortisol, cholesterol, triglycerides, epinephrine, asymmetrical dimethyl arginine. In various embodiments, the data from sensors 206 may be combined with results or detections of urinalysis to identify blood glucose, proteins, ketone, or blood in the urine, and specific gravity of urine. Values obtained from any of the foregoing measurements or units can be correlated to vascular waveform data to identify progress in therapeutic goals and/or the condition of the vasculature.

Unlike prior approaches, the integration of physiological monitoring metrics with information about vascular function, obtained either in a clinical setting or directly from the monitoring device, enables generating improved overall health assessments or health status information. Further, reports in the embodiments herein provide an explanation of the effect of all the measured physiological functions on vascular health, or overall health. Embodiments typically integrate and incorporate at least one vascular study or vascular analysis, so that an evaluation of vascular health is an integral aspect of the reporting and recommendations herein.

Figure 3:
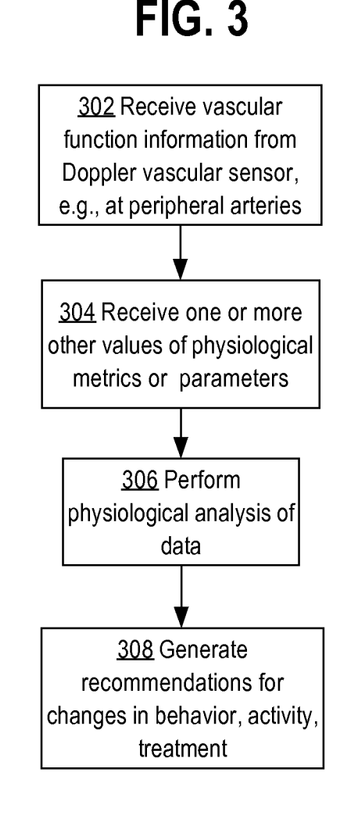
FIG. 3 illustrates an example process of generating recommendations based at least in part on vascular function information.

FIG. 3 illustrates an example process of generating recommendations based at least in part on vascular function information. At step 302, vascular function information is received from at least one Doppler vascular sensor that is used, for example, at the peripheral arteries, such as at the ankles or wrists. One of the sensors 206 typically is a Doppler vascular sensor in an embodiment and obtains the vascular function information 211, which may be received at step 302 and stored in the form of raw sensor data or as a rendered waveform or in any other form suitable for later analysis.

At step 304, the process receives one or more other values of physiological metrics or parameters. In an embodiment, values at step 304 are received through one or more other sensors 206 and may include, for example, values for one or more vital signs such as pulse, blood pressure, oxygenation, etc.

At step 306, the process performs a physiological analysis of the data that was received at steps 302, 304. Step 306 may include determining trend values ("increasing," "decreasing," etc.) based on prior measurements from the same device, or whether the current magnitude of a particular value has crossed a particular threshold that is associated with a particular physiological condition or change or is associated with a particular qualitative or quantitative descriptor or condition, for example, "elevated", "normal", "baseline", "exceptional," "average," "severe," etc.

At step 306, the process generates one or more recommendations for changes in behavior, activity, or treatment. Recommendations may comprise reports or protocols and may be based on stored tables that map the values obtained at step 302, step 304 to particular recommendations, reports, or protocols. Step 306 also may include computation such as determining whether a particular value is greater or less than values stored in the tables, and/or comparing particular trend values to corresponding trend indicators stored in the tables. Data representations other than tables may be used.

Overview of Example Uses

For the purposes of illustrating clear examples, in various embodiments, the wireless or mobile measurement device 202 described herein may be used in one or more of the following ways. The examples refer to certain input parameters, algorithms and resulting recommendations. In one embodiment, each algorithm may be implemented using one or more computer programs or other software elements, or other computer logic, and may implement the clinical state of the art reflecting the current standard of care. However, unlike past approaches, each algorithm receives as an input at least one element of digital vascular waveform data. Thus, the approaches herein can use vascular analysis as a contributing parameter in determining a resulting recommendation. Further, the integration of vascular analysis data means that a healthcare provider can correlate the other parameter values to the vascular data to result in a better assessment of the overall health of the individual, or to provide a better clinical judgment of responsive treatment that should be considered.

In particular, an improvement provided herein is in the contribution of vascular analysis data, obtained for example from a bidirectional Doppler ultrasound measurement of the peripheral arteries, in a health assessment with other biomedical parameters. The vascular analysis data is usable in individuals who are in a health state or an unhealthy state, to recognize responses of the vasculature to the individual's health state, activity or environment. The vascular analysis data may be used to recommend personal interventions and determine how other parameter values, or the responses or interventions, may be affecting vascular structure or performance. For example, the vascular analysis data might indicate only two instances of dynamic activities of arteries, which are reflected as two "bounces" in a waveform obtained from the vascular analysis. In response, a healthcare provider might recommend a relaxation exercise, breathing exercises, increasing hydration, specific aerobic exercises, and/or self-administer a supplement or medication. A subsequent vascular analysis performed shortly thereafter might reveal that the individual has achieved three (3) "bounces", indicating improved vascular performance resulting from the relaxation exercise or other intervention as stated above.

Although some embodiments are described with reference to measuring vascular activity at peripheral arteries of the extremities, other embodiments may use measurements taken at the neck, chest wall, or other body part or location at which a Doppler vascular signal may be obtained.

The vascular analysis data may be used in combination with other apparatus such as ultrasound units that measure heart chamber activity or blood flow measurement apparatus.

Alternatively, a clinician may observe that a subject individual has elevated body temperature arising, for example, from heat exhaustion. With the availability of the vascular analysis data for the individual in addition to body temperature data, the clinician may be able to observe the effect of heat exhaustion on the vascular system. Further, the accumulation of data values from all other parameters may help explain anomalies that are seen in the waveform reflecting the vascular analysis. The combination of the vascular analysis data with other parameter values therefore permits a better global assessment of the individual and a better explanation of the individual's vascular response.

1. Use of Mobile Measurement Device to Motivate Change from Sedentary Behavior

John, a sedentary individual, is sprawled upon the couch in his living room, wearing or using a mobile monitoring device. Fortunately, in his view, his favorite television show has just begun. Based on data collected from the mobile monitoring device, John's first hour of enjoyable viewing corresponds to a reasonably normal vitality condition. However, after ingesting a rather fatty meal and continuous television viewing for three more hours, John's vitality signals begin to decline, as measured by the mobile monitoring device 202 as follows:

| Parameters: | $1^{st}$ Hour: | $4^{th}$ Hour: |
|---|---|---|
| Blood Pressure | Normal | Elevated |
| Pulse | Normal | Elevated |
| Respiration | Normal | Elevated |
| Oxygenation | Normal | Decreased |
| Nitric Oxide | Normal | Increased |
| Doppler Vascular Waveform | Moderately Severe | More Severe |

The sensors 206 process these physical changes in real-time. During hour 4, John decides to connect his mobile monitoring device 202 to his tablet computer (an example of host computer 220). In an embodiment, John couples a universal serial bus (USB) cable from his tablet computer to the mobile monitoring device 202. The mobile monitoring device 202 contains a diagnostic computer program, which is automatically downloaded to the tablet computer and begins running as part of standard USB connection operations. During execution, based on the amount of change that the sensors detected in the 3-hour period, the diagnostic program generates and displays a report (an example of recommendations 216) to recommend a beneficial change in life activity as follows:

| Algorithm Implementation & Recommendation: |
| --- |
| 1. 20 minute walking activity |
| 2. 8 fl oz. water consumption |
| 3. 2 tablet aspirin intake to relieve blood pressure |
| 4. Utilize inhaler to increase oxygenation |

In response, John ceases his laziness and follows the step by step process. He continues to use or wear the mobile monitoring device 202, and then re-connects it to his tablet computer. The diagnostic program reports the following changes in metrics or parameters:

| Parameters: | Decline: | Ascent: |
| --- | --- | --- |
| Blood Pressure | Elevated | Normal |
| Pulse | Elevated | Normal |
| Respiration | Elevated | Normal |
| Oxygenation | Decreased | Normal |
| Nitric Oxide | Increased | Normal |
| Waveform | More Severe | Baseline |

| Results: |
| --- |
| The individual's blood pressure steadily returns to normal after the intake of aspirin. The recommended use of an inhaler returns his Oxygenation and Nitric Oxide levels to stable. Drinking water decreases the flow viscosity in his vascular system. Most importantly, the waveform velocity reaches its healthy baseline value. |

2. Use of Mobile Measurement Device in Hospital Intensive Care Unit (ICU)

John was recently been admitted to the ICU. Upon arrival, healthcare providers are perplexed by John's symptoms. However, for the past day, John had been using his mobile monitoring device 202 and has it with him. One of the healthcare providers connects the mobile monitoring device 202 to a host computer 220 in the ICU, downloads or streams data from the mobile monitoring device, and uses program logic on the host computer to generate a report of the following historical parameter values that the mobile monitoring device had captured:

| Parameters: | 5 hrs prior to Arrival: | Point of Arrival: |
| --- | --- | --- |
| Blood Pressure | Normal | Major Drop |
| Nitric Oxide | Normal | Normal |
| Respiration | Normal | Increasing |
| Temperature | Normal | Increasing |
| Pulse | Normal | Increasing |
| Waveform | Baseline | Increasing Velocity |

Based on the collected data, the host program provides the following recommendation

| Algorithm Assessment: | |
| --- | --- |
| | 1. Body Inflammatory State |
| | 2. Potential Diagnosis: Sepsis |
| Action | Skin infection diagnosis and treatment. Perform blood cultures. Increase antibiotics. |

The healthcare provider evaluates the assessment and recommended action, and decides to perform the recommended actions. As a result, the following physiological effects are observed:

| Results: |
| --- |
| Patient temperature returns to normal. Nitric oxide returns to normal. Pulse returns to normal. Blood Pressure becomes normalized. Temperature cools down. Waveform velocity returns to normal. |

3. Use of Mobile Measurement Device in Athletics

Alice, marathon runner, regularly uses her mobile monitoring device 202, which stores a data file indicating the following baseline parameters and goals:

| Parameters: | Baseline: | Goal: |
| --- | --- | --- |
| Weight | Average | Exceptional |
| Blood Pressure | Average | Above Average |
| Pulse | Average | Above Average |
| Respiration | Average | Above Average |
| Nitric Oxide | Average | Exceptional |
| Oxygen | Average | Exceptional |
| Waveform | Average | Exceptional |

Over a training period of six months, Alice periodically downloads data from her mobile measurement device 202 to her laptop computer and reviews the data using program logic on the laptop. The program logic reports that, based on the data from the mobile measurement device, her body has met her goals. She is now prepared for the big race.

During the marathon, Alice continues to use her mobile measurement device 202. The mobile measurement device 202 comprises a near-field radio transceiver 230, such as a Bluetooth transceiver, that communicates with host computers having compatible transceivers that are located at waypoints on the race route. At various waypoints, Alice's team members, healthcare providers or race officials download data from Alice's mobile measurement device 220 to laptop computers at the waypoints. Host programs on the laptop computers periodically generate reports of Alice's performance. Additionally or alternatively, the mobile measurement device 220 comprises internal program logic that can display, on a wrist-mounted display, eyewear-mounted display or other output device 240, a brief report or indication of the following results. In either alternative, the vitality sensors remain intact to ensure Alice's physical condition is suitable to continue racing:

| Distance: | Health: |
| --- | --- |
| $1^{st}$ Mile | Ok |
| $2^{nd}$ Mile | Ok |
| $3^{rd}$ Mile | Ok |

-continued

| | |
|---|---|
| 4th Mile | Ok |
| 5th Mile | Decline |

| Parameters: | Status: |
|---|---|
| Blood Pressure | Dropped below baseline |
| Pulse | Slight Increase |
| Body Temperature | Slight Increase |
| Waveform | Slight Increase |

Algorithm Assessment:

1. Individual's bodily temperature increased
2. Blood pressure is dropping
3. Pulse is increasing Algorithm Recommendation:

Subject is tending towards dehydration. Take more time at water stations. Consume more carbohydrates to replenish energy. Resume Running and decrease rate of pace slightly.

In this example, one or more of the values indicated above for Health, Status, Algorithm Assessment and Algorithm Recommendation may be represented in stored data that is maintained in the mobile monitoring device 202, but not displayed or reported to Alice. Alternatively, one or more of the metrics may be reported to Alice or using the laptop computer at the waypoints; the alternatives are design choices that may depend, for example, on the size of display that is available on Alice's device. For example, if Alice is using a wrist-mounted computer or other output device 240 that has a liquid crystal display (LCD) having limited display capability, then the metrics may be reported in more limited form. Alternatively, if Alice's mobile monitoring device 202 comprises a smartphone with a high-resolution color graphics display 250, then more elaborate reporting may be provided.

Continuing with the example, assume that Alice takes heed of the recommendations of the mobile monitoring device 202 and changes her running behavior. Thereafter, the mobile monitoring device 202 collects data indicating the following:

| Distance: | Health: |
|---|---|
| 6th Mile | Improved! |
| 7th Mile | Ok |
| 8th Mile | Ok |
| 9th Mile | Ok |
| 10th Mile | Ok |

Algorithm Assessment:

1. Vital signs are normal and stable
2. Body is adequately hydrated

Algorithm Recommendation

The body may continue further exertion!

Alice continues to review reports or indications from her mobile monitoring device 202 as she enters later stages of the race. The mobile monitoring device 202 collects data indicating the following:

| Distance: | Health: |
|---|---|
| 11th Mile | Ok |
| 12th Mile | Ok |
| 13th Mile | Ok |
| 14th Mile | Ok |
| 15th Mile | Ok |
| 16th Mile | Ok |
| 17th Mile | Ok |
| 18th Mile | Declining |
| 19th Mile | Declining |
| 20th Mile | Sharp Decline |

Algorithm Assessment:

1. Health parameters started falling after the 18th Mile.
2. Experienced a sharp decline after the 20th Mile.
3. Further analysis of parameters required:

| Parameters: | 18th Mile: | 20th Mile |
|---|---|---|
| Blood Pressure | Moderate | Severe |
| Pulse | Moderate | Severe |
| Respiration | Moderate | Severe |
| Body Temperature | Moderate | Severe |
| Waveform | Moderate | Severe |

| Ambient Temperature | Sharp decrease in humidity |
|---|---|

Algorithm Assessment:

1. All Parameters are experiencing a sharp decline.
2. Further Decline is hazardous.
3. Individual is severely dehydrated.

Algorithm Recommendation:

1. Halt running immediately.
2. Consume water and carbs to replenish body.
3. Continue walking until vitality signals increase.

Results:

Because it was much hotter towards the end of the race, our athlete experienced severe dehydration at her 20th mile. Without her vitality sensors, there would be no way to accurately determine her state of condition and hydration.

In each of the preceding examples, the metric "Waveform" represents data obtained from at least one vascular sensor 206 and is based on bidirectional waveform analysis. "Bidirectional" refers to the fact that in normal circulation, blood is pumped and flows in a first direction through a blood vessel, then briefly reverses direction, and then is pumped and flows again in the first direction. For example, a miniaturized Doppler vascular sensor may be used as one of the sensors 206 to generate and store data representing an acoustic waveform based on detecting the flow of blood in one or more blood vessels. This data is indicative of the elasticity of the blood vessels, among other metrics; for example, a wider waveform is observed to indicate greater elasticity of the walls of the blood vessels, larger volume of blood flow, or a thinner waveform is observed to indicate lesser volume and less elasticity, at least at the measurement site, and greater elasticity is associated with reduced risk of certain major diseases such as CVD, diabetes and respiratory ailments. Through data collection, observation of velocity and volume of waveform of the first, second, third, and sometimes a fourth waveform, the processes herein will be able to correlate more accurately the status of physiological responses. The inventor fundamentally has recognized that combining vascular function information 211 representing vascular condition with one or more other physiological metrics 212 will provide a better capability for evaluating overall health of an individual and for providing recommendations for activity or treatment. Further, the integration of vascular bidirectional waveform analysis data representing vascular condition with a plurality of other physiological metrics will provide a superior capability for evaluating overall health of an individual and for providing recommendations for activity or treatment. Still further, having multiple examples of vascular data available over a long period of time can provide better environmental information on which health assessments may be based.

Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 1:
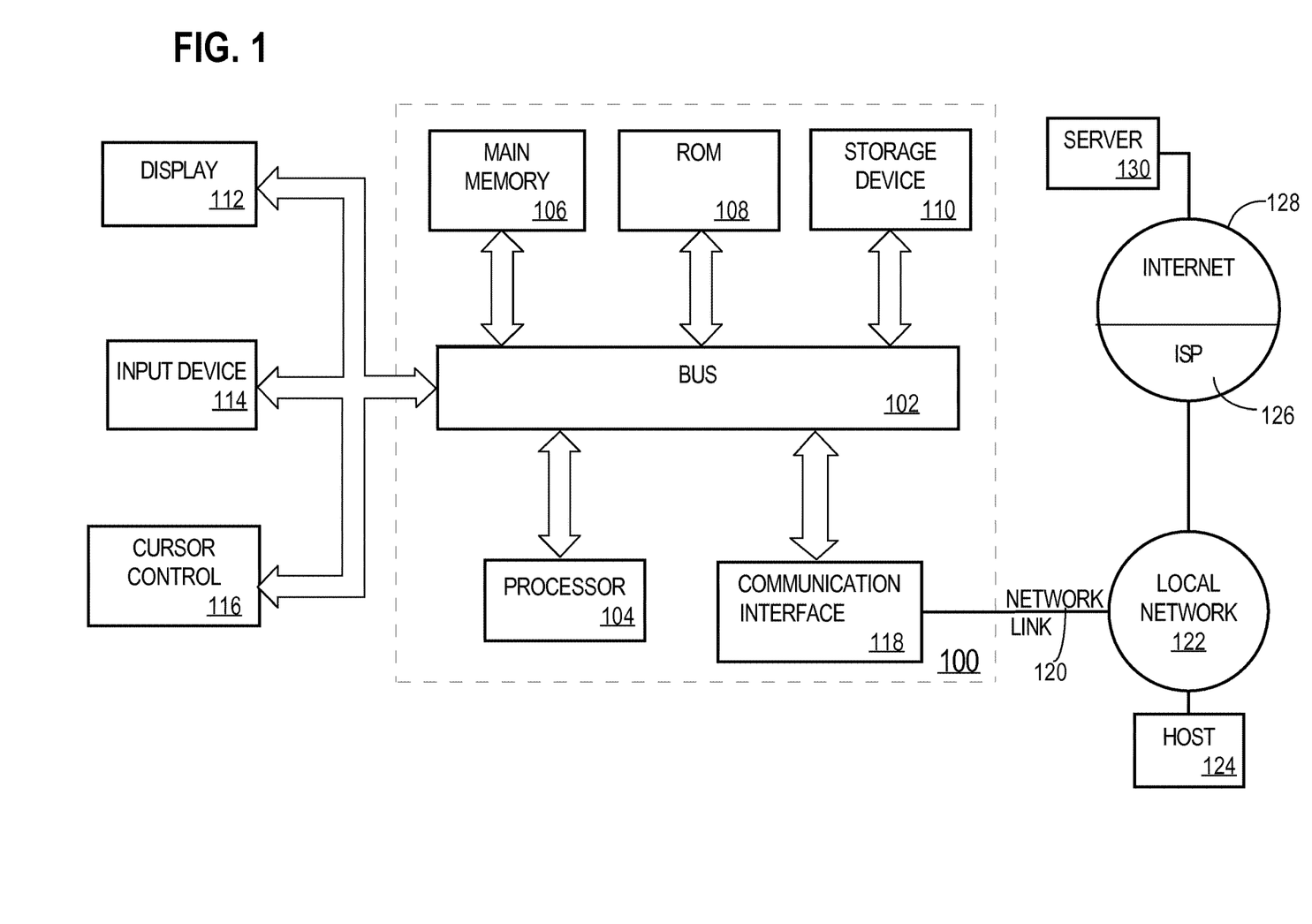
FIG. 1 is a block diagram that illustrates a computer system upon which an embodiment of the invention may be implemented.

For example, FIG. 1 is a block diagram that illustrates a computer system 100 upon which an embodiment of the invention may be implemented. Computer system 100 includes a bus 102 or other communication mechanism for communicating information, and a hardware processor 104 coupled with bus 102 for processing information. Hardware processor 104 may be, for example, a general purpose microprocessor.

Computer system 100 also includes a main memory 106, such as a random access memory (RAM) or other dynamic storage device, coupled to bus 102 for storing information and instructions to be executed by processor 104. Main memory 106 also may be used for storing temporary variables or other intermediate information during execution of instructions to be executed by processor 104. Such instructions, when stored in non-transitory storage media accessible to processor 104, render computer system 100 into a special-purpose machine that is customized to perform the operations specified in the instructions.

Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT), for displaying information to a computer user. An input device 114, including alphanumeric and other keys, is coupled to bus 102 for communicating information and command selections to processor 104. Another type of user input device is cursor control 116, such as a mouse, a trackball, or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

Computer system 100 may implement the techniques described herein using customized hard-wired logic, one or more ASICs or FPGAs, firmware and/or program logic which in combination with the computer system causes or programs computer system 100 to be a special-purpose machine. According to one embodiment, the techniques herein are performed by computer system 100 in response to processor 104 executing one or more sequences of one or more instructions contained in main memory 106. Such instructions may be read into main memory 106 from another storage medium, such as storage device 110. Execution of the sequences of instructions contained in main memory 106 causes processor 104 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 110. Volatile media includes dynamic memory, such as main memory 106. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 102. Transmission media can also take the form of acoustic or light waves, such as those generated during radio-wave and infra-red data communications.

Various forms of media may be involved in carrying one or more sequences of one or more instructions to processor 104 for execution. For example, the instructions may initially be carried on a magnetic disk or solid state drive of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector can receive the data carried in the infra-red signal and appropriate circuitry can place the data on bus 102. Bus 102 carries the data to main memory 106, from which processor 104 retrieves and executes the instructions. The instructions received by main memory 106 may optionally be stored on storage device 110 either before or after execution by processor 104.

Computer system 100 also includes a communication interface 118 coupled to bus 102. Communication interface 118 provides a two-way data communication coupling to a network link 120 that is connected to a local network 122. For example, communication interface 118 may be an integrated services digital network (ISDN) card, cable modem, satellite modem, or a modem to provide a data communication connection to a corresponding type of telephone line. As another example, communication interface 118 may be a local area network (LAN) card to provide a data communication connection to a compatible LAN. Wireless links may also be implemented. In any such implementation, communication interface 118 sends and receives electrical, electromagnetic or optical signals that carry digital data streams representing various types of information.

Network link 120 typically provides data communication through one or more networks to other data devices. For example, network link 120 may provide a connection through local network 122 to a host computer 124 or to data equipment operated by an Internet Service Provider (ISP) 126. ISP 126 in turn provides data communication services through the world wide packet data communication network now commonly referred to as the "Internet" 128. Local network 122 and Internet 128 both use electrical, electromagnetic or optical signals that carry digital data streams. The signals through the various networks and the signals on network link 120 and through communication interface 118, which carry the digital data to and from computer system 100, are example forms of transmission media.

Computer system 100 can send messages and receive data, including program code, through the network(s), network link 120 and communication interface 118. In the Internet example, a server 130 might transmit a requested code for an application program through Internet 128, ISP 126, local network 122 and communication interface 118.

The received code may be executed by processor 104 as it is received, and/or stored in storage device 110, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A mobile measurement device comprising:
   a computing device comprising one or more processors;
   non-transitory storage media storing instructions, wherein the non-transitory storage media is coupled to the computing device;
   a first output device that is coupled to the computing device; and
   one or more first sensors that:
      are coupled to the computing device using one or more corresponding compatible digital interfaces, and
      are configured for attachment to peripheral artery locations of a human body,
   wherein the one or more first sensors comprise at least one ultrasound sensor;
   wherein, in conjunction with the at least one ultrasound sensor, the computing device is configured to:
      acoustically measure blood flow in a blood vessel,
      cooperate with the stored instructions to perform bidirectional waveform Doppler ultrasound analysis and determine an elasticity of vascular walls of the blood vessel from the bidirectional waveform Doppler ultrasound analysis,
      provide output waveform data representing the acoustic measurements of blood flow in the blood vessel, and
   wherein the stored instructions are configured to determine one or more recommendations of treatment based upon, at least in part, the measured blood flow and the bidirectional waveform Doppler ultrasound analysis and, when executed by the computing device, cause the computing device to perform:
      receiving a digital Doppler vascular signal from the at least one ultrasound sensor;
      based at least in part on the digital Doppler vascular signal, determining one or more first parameters comprising vascular function information that reflects the elasticity of vascular walls;
      determining one or more second parameters comprising one or more of blood pressure, pulse, respiration, oxygenation, glucose level and nitric oxide level;
      detecting when changes in the magnitude of values from the vascular function information cross a particular threshold;
      in response to detecting that changes in the magnitude of values from the vascular function information cross the particular threshold, generating the one or more recommendations of treatment, based on:
         the one or more first parameters, and
         the one or more second parameters,
      wherein the one or more recommendations of treatment comprise one or more reports or protocols, and
      wherein determining the one or more recommendations of treatment comprises looking up the one or more reports or protocols based on a mapping from the one or more first parameters and the one or more second parameters to the one or more reports or protocols; and
      displaying the one or more recommendations of treatment on the first output device, wherein the first output device is a wrist-mounted display.

2. The mobile measurement device of claim 1 wherein the computing device comprises any of: a smartphone, a tablet computer, and a laptop computer.

3. The mobile measurement device of claim 1 further comprising one or more second sensors that:
   are coupled to the computing device using one or more corresponding compatible digital interfaces, and
   are configured for attachment to peripheral artery locations of a human body,
   the one or more second sensors comprising one or more of:
      a carbon dioxide sensor, or
      a nitric oxide sensor.

4. The mobile measurement device of claim 1 wherein the one or more reports or protocols comprise any of: a protocol for exercise, a protocol for sports performance, a protocol for changes in patient lifestyle, a protocol for patient stress management.

5. The mobile measurement device of claim 1, further comprising:
   a radio-frequency transceiver coupled to the computing device, and
   a second output device that is coupled to the computing device, where the second output device is a computer display unit.

6. The mobile measurement device of claim 1, wherein the stored instructions are further configured to cause the computing device to perform:
   making a first determination whether levels of one or more of blood pressure, pulse, or rate of respiration are elevated;
   making a second determination whether nitric oxide as measured in blood or rate of respiration has increased;
   making a third determination whether a change in the magnitude of a Doppler vascular waveform velocity crosses a particular threshold; and
   in response to the first, second, and third determinations all being affirmative, generating recommendations for exercise, water consumption, and aspirin consumption.

7. The device of claim 1, wherein the computing device comprises a steering wheel of a motor vehicle.

8. The device of claim 1, wherein the computing device comprises any of a ring-mounted computer, a hat-mounted computer, a helmet-mounted computer, and an eyewear-mounted computer.

9. A data processing system comprising:
a portable physiological measuring device configured for attachment to a human body of a patient, for receiving and storing data representing one or more physiological parameters of the patient;
one or more Doppler vascular first sensors configured for attachment to peripheral artery locations of the body;
a portable Doppler vascular signal measuring device coupled to the Doppler vascular first sensors;
a mobile computing device, comprising one or more processors, configured to interface to the Doppler vascular signal measuring device and to the physiological measuring device;
an output device that is coupled to the mobile computing device;
non-transitory storage media storing instructions, wherein the non-transitory storage media is coupled to the mobile computing device,
wherein, in conjunction with the one or more Doppler vascular first sensors, the mobile computing device is configured to:
acoustically measure blood flow in a respective blood vessel,
under control of the instructions, perform bidirectional waveform Doppler ultrasound analysis and determine an elasticity of vascular walls of the blood vessel from the bidirectional waveform Doppler ultrasound analysis,
provide output waveform data representing acoustic measurements of blood flow in the blood vessel; and
a network interface in the mobile computing device configured to couple to a data network for communication of patient data from the portable physiological measuring device and the Doppler vascular signal measuring device to the mobile computing device,
wherein the stored instructions are configured to determine one or more recommendations of treatment based upon, at least in part, the measured blood flow and the bidirectional waveform Doppler ultrasound analysis and, when executed by the computing device, cause the mobile computing device to perform:
determining values of the one or more physiological parameters of the patient, based on data received from the portable physiological measuring device;
receiving a digital Doppler vascular signal from the at least one Doppler vascular signal measuring device;
based at least in part on the digital Doppler vascular signal, determining vascular function information based on data received from the Doppler vascular signal measuring device;
wherein the vascular function information reflects the elasticity of vascular walls;
detecting when changes in the magnitude of values from the vascular function information cross a particular threshold;
in response to detecting that changes in the magnitude of values from the vascular function information cross the particular threshold, generating
the one or more recommendations of treatment, based on;
the vascular function information, and
the one or more physiological parameters of the patient,
wherein the one or more recommendations of treatment comprise one or more reports or protocols, and
wherein determining the one or more recommendations of treatment comprises looking up the one or more reports or protocols based on a mapping from the vascular function information and the one or more physiological parameters of the patient to the one or more reports or protocols; and
displaying the one or more recommendations of treatment on the output device, wherein the output device is a wrist-mounted display.

10. The system of claim 9 wherein the mobile computing device comprises any of: a smartphone, a tablet computer, and a laptop computer.

11. The system of claim 9 wherein:
the portable physiological measuring device comprises one or more second sensors configured for attachment to peripheral artery locations of the body, and
the one or more second sensors comprise one or more of: a carbon dioxide sensor or a nitric oxide sensor.

12. The system of claim 9 wherein the one or more reports or protocols comprise any of: a protocol for sports performance, a protocol for changes in patient lifestyle, or a protocol for patient stress management.

13. The system of claim 9 wherein the physiological measuring device comprises an electrocardiogram (ECG) apparatus and wherein generating the one or more recommendations of treatment is based on ECG data and the vascular function information.

14. The system of claim 9, wherein the mobile computing device comprises a steering wheel of a motor vehicle.

15. The system of claim 9, wherein the mobile computing device comprises any of a ring-mounted computer, a hat-mounted computer, a helmet-mounted computer, and an eyewear-mounted computer.

\* \* \* \* \*